US011130728B2

(12) United States Patent
Tsuda

(10) Patent No.: US 11,130,728 B2
(45) Date of Patent: Sep. 28, 2021

(54) CARBONATE DERIVATIVE PRODUCTION METHOD

(71) Applicants: NATIONAL UNIVERSITY CORPORATION KOBE UNIVERSITY, Hyogo (JP); MITSUBISHI GAS CHEMICAL COMPANY, INC., Tokyo (JP)

(72) Inventor: Akihiko Tsuda, Hyogo (JP)

(73) Assignees: NATIONAL UNIVERSITY CORPORATION KOBE UNIVERSITY, Hyogo (JP); MITSUBISHI GAS CHEMICAL COMPANY, INC., Tokyo (JP)

( * ) Notice: Subject to any disclaimer, the term of this patent is extended or adjusted under 35 U.S.C. 154(b) by 63 days.

(21) Appl. No.: 16/608,898

(22) PCT Filed: Apr. 27, 2018

(86) PCT No.: PCT/JP2018/017348
§ 371 (c)(1),
(2) Date: Oct. 28, 2019

(87) PCT Pub. No.: WO2018/211952
PCT Pub. Date: Nov. 22, 2018

(65) Prior Publication Data
US 2020/0079723 A1     Mar. 12, 2020

(30) Foreign Application Priority Data

May 16, 2017   (JP) .............................. JP2017-097681

(51) Int. Cl.
*C07D 317/38* (2006.01)
*C07C 68/00* (2020.01)
(Continued)

(52) U.S. Cl.
CPC .............. *C07C 68/00* (2013.01); *C07B 61/00* (2013.01); *C07D 317/38* (2013.01); *C07D 317/64* (2013.01); *C08G 64/06* (2013.01)

(58) Field of Classification Search
CPC ..... C07C 68/00; C07C 329/20; C07C 201/12; C07C 273/1809; C07C 2601/14;
(Continued)

(56) References Cited

U.S. PATENT DOCUMENTS

2016/0032046 A1   2/2016  Shirota et al.

FOREIGN PATENT DOCUMENTS

| JP | 7-10811 | 1/1995 |
| JP | 10-291965 | 11/1998 |

(Continued)

OTHER PUBLICATIONS

Extended European Search Report dated Nov. 12, 2020 in corresponding European Patent Application No. 18802405.3.
(Continued)

*Primary Examiner* — Taylor V Oh
(74) *Attorney, Agent, or Firm* — Wenderoth, Lind & Ponack, L.L.P.

(57) ABSTRACT

The objective of the present invention is to provide a method for producing a carbonate derivative in a safe and efficient manner. The method for producing a carbonate derivative according to the present invention is characterized in comprising irradiating light on a composition containing a $C_{1-4}$ halogenated hydrocarbon having one or more kinds of halogen atoms selected from the group consisting of a chlorine atom, a bromine atom and an iodine atom, a nucleophilic functional group-containing compound and the specific base in the presence of oxygen.

9 Claims, 1 Drawing Sheet

(51) Int. Cl.
*C07B 61/00* (2006.01)
*C07D 317/64* (2006.01)
*C08G 64/06* (2006.01)

(58) Field of Classification Search
CPC .... C07B 61/00; C07D 317/38; C07D 317/64;
C07D 233/56; C07D 317/46; C08G
64/06; C08G 71/02; C08G 64/0208;
C08G 64/305; C08G 64/307; C08G 64/04
USPC .......................................................... 549/230
See application file for complete search history.

(56) References Cited

FOREIGN PATENT DOCUMENTS

| JP | 2001-129397 | | 5/2001 |
| JP | 2013-181028 | | 9/2013 |
| JP | 2013181028 | * | 9/2013 |
| WO | 2014/171367 | | 10/2014 |

OTHER PUBLICATIONS

Kuwahara et al., "Photochemical molecular storage of $Cl_2$, HCl, and $COCl_2$: Synthesis of organochlorine compounds, salts, ureas, and polycarbonate with photodecomposed chloroform", Organic Letters, 2012, vol. 14, NB. 13, pp. 3376-3379, XP055745410.

Kuwahara et al., "Photochemical molecular storage of Cl2, HCl, and COCl2: Synthesis of organochlorine compounds, salts, ureas, and polycarbonate with photodecomposed chloroform", Organic Letters, 2012, vol. 14, NB. 13, pp. 3376-3379, XP055745415.

International Search Report dated Jul. 17, 2018 in International (PCT) Application No. PCT/JP2018/017348.

Okuma et al., "Detection of aromatic primary amines by a photochemical reaction with pyridine", The Journal of the Japan Society for Analytical Chemistry, vol. 24, Jan. 1975, pp. 385-387, with partial translation, cited in Specification.

Tsurugi et al., Journal of the Society of Rubber Science and Technology, vol. 43, No. 5, 1970, pp. 337-346, with partial translation, cited in Specification.

Herbich et al., "Mechanisms of fluorescence quenching by hydrogen bonding in various aza aromatics", J. Photochem. Photobiol. A: Chem., vol. 80, 1994, pp. 157-160.

Kuwahara et al., "Photochemical molecular storage of $Cl_2$, HCl, and $COCl_2$: Synthesis of organochlorine compounds, salts, ureas, and polycarbonate with photodecomposed chloroform", Organic Letters, vol. 14, No. 13, 2012, pp. 3376-3379.

Kuwahara et al., "Photo-recycling reactions of Halomethanes (I): Synthesis of Urea Derivatives from Chloroform and Primary Amines", Abstracts of the meeting of The Chemical Society of Japan, 92nd, 2012, p. 1251, 2 K2-14, with partial translation, cited in ISR.

Kuwahara et al., "Photo-recycling reactions of Halomethanes (2): Synthesis of Carbonate Derivatives from Chloroform and Phenol Derivatives", Abstracts of the meeting of The Chemical Society of Japan, 92nd, 2012, p. 1251, 2 K2-14, with partial translation, cited in ISR.

Singapore Search Report and Written Opinion dated Feb. 11, 2021 in Singaporean Patent Application No. 11201909670Y.

Search Report and Office Action dated Jun. 15, 2021 in corresponding Russian Patent Application No. 2019138715, with English Translation.

* cited by examiner

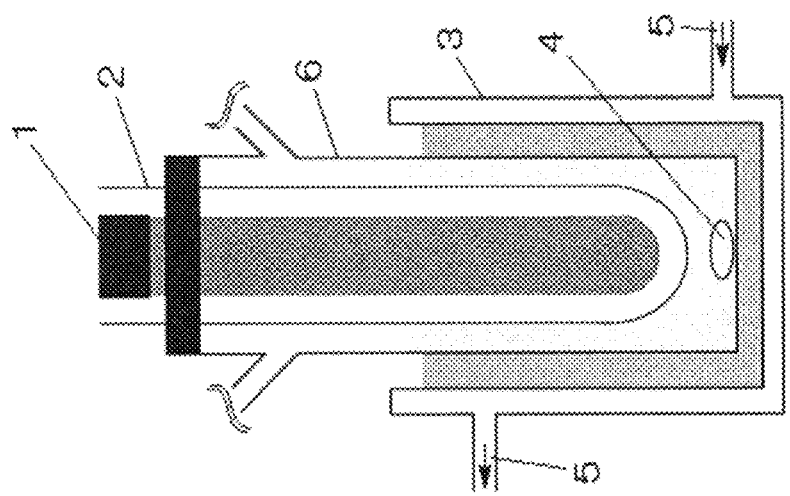

CARBONATE DERIVATIVE PRODUCTION METHOD

TECHNICAL FIELD

The present invention relates to a method for producing a carbonate derivative in a safe and efficient manner.

BACKGROUND ART

A linear carbonate among a carbonate derivative has been conventionally used as a solvent or the like. In particular, a production amount of a linear carbonate is recently increased as a non-aqueous solvent for a lithium-ion secondary battery electrolyte. A polycarbonate is prepared by reacting carbonic acid with a bisphenol compound and is widely used as an engineering plastic excellent in transparency and impact resistance. A urea resin is widely used as a material for an adhesive and a dish. A polydithiocarbonate is expected as a stable optical material with low coloration.

A carbonate derivative is generally produced from phosgene and a nucleophilic functional group-containing compound. Phosgene is very toxic. For example, phosgene is easily reacted with water to generate hydrogen chloride and has a history of being used as a poison gas. In addition, a carbonate derivative is produced through a reaction of carbon monoxide, an alcohol and oxygen, but this method has a problem that toxic carbon monoxide has to be used under a high pressure. Accordingly, various safe methods for producing a carbonate ester and a polycarbonate have been studied.

For example, a method for producing a target carbonate derivative by subjecting a carbonate ester to a transesterification reaction in the presence of a catalyst is described in Patent document 1. This method, however, does not provide a fundamental solution, since there remains the problem of how to prepare a carbonate derivative as a raw material compound in this method. This method also has problems of a use of an expensive catalyst and of a reverse reaction and a side reaction due to a residual catalyst.

A method for producing a carbonate derivative from an epoxy compound and carbon dioxide in the presence of a catalyst is disclosed in Patent document 2. It is not needed in this method to use phosgene and carbon monoxide. But this method is not suitable for an industrial mass production, since it is needed to use an expensive catalyst and adjust a pressure of carbon dioxide to high.

The present inventor has developed a method for producing a halogenated carbonate ester by subjecting a halogenated hydrocarbon and an alcohol to an oxidative photoreaction (Patent document 3) and a method for producing a halogenated formate ester which method contains the steps of obtaining a mixture of phosgene by irradiating light on chloroform in the presence of oxygen and reacting an alcohol with the mixture without isolating the phosgene (Patent document 4).

PRIOR ART DOCUMENT

Patent Document

Patent document 1: JP H7-10811 A
Patent document 2: JP 2001-129397 A
Patent document 3: WO 2014/171367
Patent document 4: JP 2013-181028 A

Non-Patent Document

Non-patent document 1: OKUMA Seiichi et al., The journal of the Japan Society for Analytical Chemistry, Vol. 24, pp. 385-387 (1975)
Non-patent document 2: TSURUGI Jitsuo et al., Journal of the Society of Rubber Science and Technology, Japan, Vol. 43, Number 5, pp. 337-346 (1970)
Non-patent document 3: Jerzy Herbich et al., J. Photochem. Photobiol. A: Chem., 80, pp. 157-160 (1994)

DISCLOSURE OF THE INVENTION

Problems to be Solved by the Invention

In general, phosgene is used for producing a carbonate derivative as described above. Even a production method without using phosgene has a problem that other toxic compound or an expensive catalyst has to be used or phosgene has to be used for producing a raw material compound.

Under the above-described circumstances, the objective of the present invention is to provide a method for producing a carbonate derivative in a safe and efficient manner.

Means for Solving the Problems

The inventor of the present invention made extensive studies to solve the above problems. As a result, the inventor completed the present invention by finding that a carbonate derivative can be amazingly produced in a safe and efficient manner by subjecting a halogenated hydrocarbon compound and the specific nucleophilic functional group-containing compound to a photoreaction in the presence of oxygen and the specific base. Since it has been generally known that an organic base forms a pigment by a photoreaction, plays a role as an antioxidant to capture a radical and quenches the fluorescence of a compound by a mechanism such as an electron transfer, and pyridine is broken down into glutaconaldehyde or the like due to ultraviolet (Non-patent documents 1 to 3), it has been predicted that an organic base is disadvantageous for a photoreaction such as the inventions by the inventor described in Patent document 3 and Patent document 4. On the one hand, it is very surprising that a carbonate derivative is efficiently generated by a photoreaction in the presence of the specific base.

Hereinafter, the present invention is described.

[1] A method for producing a carbonate derivative, comprising
irradiating light on a composition containing a $C_{1-4}$ halogenated hydrocarbon having one or more kinds of halogen atoms selected from the group consisting of a chlorine atom, a bromine atom and an iodine atom, a nucleophilic functional group-containing compound and a base in the presence of oxygen,
wherein the nucleophilic functional group-containing compound is represented by the following formula (i) and the carbonate derivative is a linear carbonate derivative represented by the following formula (I), or
the nucleophilic functional group-containing compound is represented by the following formula (ii) and the carbonate derivative is a polycarbonate derivative containing a unit represented by the following formula (II-1) or a cyclic carbonate derivative represented by the following formula (II-2), and wherein the base is one or more bases selected from the group essentially consisting of a heterocyclic aromatic amine, a non-nucleophilic strong base and an inorganic base.

R¹—A—H    (i)

H—A—R²—A—H    (ii)

R¹—A—C(=O)—A—R¹    (I)

[—A—R²—A—C(=O)—]    (II-1)

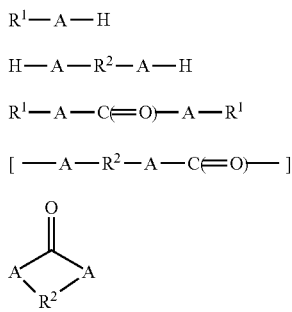

(II-2)

wherein

A is O, S or NR³ wherein R³ is H or a $C_{1-4}$ alkyl group, or R³ forms a nitrogen-containing heterocyclic group with R¹ and N, R¹ is a $C_{6-14}$ aryl group, a $C_{4-14}$ heteroaryl group or a $C_{2-24}$ alkylpolyoxyalkylene group, R² is a $C_{2-10}$ alkylene group, a $C_{6-14}$ arylene group, a $C_{4-14}$ heteroarylene group or a $C_{2-24}$ polyoxyalkylene group.

[2] The production method according to the above [1], wherein the $C_{1-4}$ halogenated hydrocarbon is a $C_{1-4}$ polyhalogenated hydrocarbon.

[3] The production method according to the above [1], wherein the $C_{1-4}$ halogenated hydrocarbon is chloroform.

[4] The production method according to any one of the above [1] to [3], wherein the heterocyclic aromatic amine is pyridine, picoline or lutidine.

[5] The production method according to any one of the above [1] to [4], wherein the non-nucleophilic strong base is 1,5,7-triazabicyclo[4.4.0]dec-5-ene, 7-methyl-1,5,7-triazabicyclo[4.4.0]dec-5-ene, 1,8-diazabicyclo[5.4.0]undec-7-ene, 1,5-diazabicyclo[4.3.0]non-5-ene or 1,1,3,3-tetramethylguanidine.

[6] The production method according to any one of the above [1] to [5], wherein the inorganic base is an alkali metal hydroxide, an alkali metal hydrogen carbonate or an alkali metal carbonate.

[7] The production method according to any one of the above [1] to [6], wherein 0.001 times or more by mole and 1 time or less by mole of the nucleophilic functional group-containing compound is used to the $C_{1-4}$ halogenated hydrocarbon.

[8] The production method according to any one of the above [1] to [7], wherein 1.5 times or more by mole and 10 times or less by mole of the base is used to the nucleophilic functional group-containing compound.

[9] The production method according to any one of the above [1] to [8], wherein a wavelength of the light irradiated on the composition is 180 nm or more and 500 nm or less.

Effect of the Invention

It is not needed in the present invention method that an expensive catalyst and an extremely toxic compound such as phosgene and carbon monoxide are used as a raw material compound. Thus, the present invention method is industrially very useful as a technology to produce a useful carbonate derivative in a safe and efficient manner.

BRIEF DESCRIPTION OF THE DRAWINGS

FIG. 1 is a schematic picture to demonstrate an example of a reaction device usable in the present invention method.

MODE FOR CARRYING OUT THE INVENTION

In the method for producing a carbonate derivative according to the present invention, light is irradiated on a composition containing a $C_{1-4}$ halogenated hydrocarbon having one or more kinds of halogen atoms selected from the group consisting of a chlorine atom, a bromine atom and iodine atom, a nucleophilic functional group-containing compound and the specific base in the presence of oxygen.

1. $C_{1-4}$ Halogenated Hydrocarbon

In the reaction of the present invention, a $C_{1-4}$ halogenated hydrocarbon may be decomposed due to the irradiated light and oxygen into a halogenated carbonyl or a halogenated carbonyl-like compound and reacted with a hydroxy group-containing compound to generate a carbonate derivative. Even if a toxic halogenated carbonyl is generated, such a halogenated carbonyl is immediately reacted with a hydroxy group-containing compound due to an extremely high reactivity. As a result, a halogenated carbonyl does not leak to out of the reaction mixture or if a halogenated carbonyl leaks out, the leakage amount is small. For example, a strict restriction is imposed on the transportation of phosgene, since phosgene among a halogenated carbonyl is highly toxic; on the one hand, a $C_{1-4}$ halogenated hydrocarbon is of course not so dangerous. The reaction according to the present invention may not be possibly mediated by a halogenated carbonyl or a halogenated carbonyl-like compound, since the reaction proceeds even in the presence of an inorganic base aqueous solution as described later.

A $C_{1-4}$ halogenated hydrocarbon which is liquid under an atmospheric temperature and an atmospheric pressure is used as an organic solvent or the like in a large amount but when released to the atmosphere, causes environmental pollution such as air pollution and ozone layer destruction. The present invention is a technology to produce a useful compound by a photolysis of a $C_{1-4}$ halogenated hydrocarbon and greatly contributes to both an industry and an environmental science.

The $C_{1-4}$ halogenated hydrocarbon is an alkane, an alkene or an alkyne which have a carbon number of 1 or more and 4 or less and which is substituted by one or more halogen atoms selected from the group consisting of a chlorine atom, a bromine atom and an iodine atom. As described above, the $C_{1-4}$ halogenated hydrocarbon may be decomposed by an irradiated light and oxygen and may act similarly to a halogenated carbonyl in the present invention. The $C_{1-4}$ halogenated hydrocarbon is preferably a $C_{1-2}$ halogenated hydrocarbon, and more preferably a halogenated methane. When the carbon number is 2 or more and 4 or less, the $C_{1-4}$ halogenated hydrocarbon is preferably an alkene or an alkyne having one or more unsaturated bonds in order to be decomposed more easily. In addition, it is preferred that the $C_{1-4}$ halogenated hydrocarbon has two or more of the above-described halogen atoms. Furthermore, a $C_{1-4}$ polyhalogenated hydrocarbon having two or more of the above-described halogen atoms on the same carbon is preferred, though the above-described halogen atom is transferred with the decomposition.

As the specific $C_{1-4}$ halogenated hydrocarbon, a $C_{1-4}$ halogenated alkane, a $C_{2-4}$ halogenated alkene or a $C_{2-4}$ halogenated alkyne is preferred, a halogenated methane, a halogenated ethene or a halogenated acetylene is more preferred in terms of an easy generation of a halogenated carbonyl-like compound, a polyhalogenated methane, a polyhalogenated ethene or a polyhalogenated acetylene having two or more of the above-described halogen atoms is particularly preferred, and a polyhalogenated methane is the most preferred. An example of the $C_{1-4}$ halogenated hydrocarbon includes a halogenated methane such as dichloromethane, chloroform, dibromomethane, bromoform, iodomethane and diiodomethane; a halogenated ethane such as 1,1,2-trichloroethane, 1,1,1-trichloroethane, 1,1,2,2-tetrachloroethane and 1,1,1,2-tetrachloroethane; a halogenated propane such as 1,1,1,3-tetrachloropropane; a perhalogenated alkane such as tetrachloromethane, tetrabromomethane, tetraiodomethane, hexachloroehane and hexabromoethane; a perhalogenated ethene such as 1,1,2,2-tetrachloroethene and 1,1,2,2-tetrabromoethene.

The $C_{1-4}$ halogenated hydrocarbon may be appropriately selected depending of the target reaction and the desired product. One $C_{1-4}$ halogenated hydrocarbon may be used alone, or two or more of the $C_{1-4}$ halogenated hydrocarbons may be used in combination. It is preferred that only one $C_{1-4}$ halogenated hydrocarbon is used depending on the target compound. The $C_{1-4}$ halogenated hydrocarbon having a chloro group is preferred.

The $C_{1-4}$ halogenated hydrocarbon usable in the present invention method may be a $C_{1-4}$ halogenated hydrocarbon which has been once used as, for example, a solvent. It is preferred that such a used $C_{1-4}$ halogenated hydrocarbon is purified to some extent for use, since if a large amount of an impurity and water is contained, the reaction may be possibly inhibited. For example, it is preferred that water and a water-soluble impurity are removed by washing with water and then the $C_{1-4}$ halogenated hydrocarbon is dried by anhydrous sodium sulfate, anhydrous magnesium sulfate or the like. An excessive purification by which the productivity becomes less is not needed, since even when water is contained, the reaction may proceed. The water content is preferably 0.5 vol % or less, more preferably 0.2 vol % or less, and even more preferably 0.1 vol % or less. The $C_{1-4}$ halogenated hydrocarbon to be reused may contain a degradant of the $C_{1-4}$ halogenated hydrocarbon.

2. Nucleophilic Functional Group-Containing Compound

The "nucleophilic functional group-containing compound" in the present invention is a compound which has a nucleophilic functional group containing a nucleophilic oxygen atom, sulfur atom and/or nitrogen atom and which is represented by the formula (i) or the formula (ii). The compound is respectively abbreviated as "nucleophilic functional group-containing compound (i)" or "nucleophilic functional group-containing compound (ii)" in some cases. The nucleophilic functional group-containing compound used in the present invention does not have a fluorine atom as a substituent group; and as a result, the carbonate derivative produced by the present invention method also does not have a fluorine atom as a substituent group. The specific nucleophilic functional group-containing compound is used in the present invention; therefore, the reaction proceeds until the carbonate derivative is obtained.

When the nucleophilic functional group-containing compound (i) is used in the present invention, the obtained carbonate derivative is the linear carbonate represented by the formula (I), which is abbreviated as "linear carbonate (I)" in some cases. When the hydroxy group-containing compound (ii) is used, the obtained carbonate derivative is the polycarbonate derivative containing the unit represented by the formula (II-1), which is abbreviated as "polycarbonate derivative (II-1)" in some cases, or the cyclic carbonate derivative represented by the formula (II-2), which is abbreviated as "cyclic carbonate derivative (II-2)" in some cases.

The nucleophilic functional group-containing compound (i) and nucleophilic functional group-containing compound (ii) used in the present invention production method as the raw material compound and the linear carbonate derivative (I), polycarbonate derivative (II-1) and cyclic carbonate derivative (II-2) as the target compound are described as follows.

 (i)

 (ii)

 (I)

 (II-1)

 (II-2)

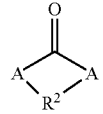

wherein

A is O, S or $NR^3$ wherein $R^3$ is H or a $C_{1-4}$ alkyl group, or $R^3$ forms a nitrogen-containing heterocyclic group with $R^1$ and N, $R^1$ is a $C_{6-14}$ aryl group, a $C_{4-14}$ heteroaryl group or a $C_{2-24}$ alkylpolyoxyalkylene group, $R^2$ is a $C_{2-10}$ alkylene group, a $C_{6-14}$ arylene group, a $C_{4-14}$ heteroarylene group or a $C_{2-24}$ polyoxyalkylene group.

In this disclosure, a halogenated hydrocarbon having 1 or more and 4 or less carbon atoms is described as a "$C_{1-4}$ halogenated hydrocarbon". Other groups and compounds are similarly described.

The $R^3$ in the nucleophilic functional group-containing compound (i) is preferably H. The nitrogen-containing heterocyclic group formed by $R^1$, $R^3$ and N may be a non-aromatic nitrogen-containing heterocyclic group or an aromatic nitrogen-containing heterocyclic group. An example of the non-aromatic nitrogen-containing heterocyclic group includes pyrrolidinyl and piperidinyl. An example of the aromatic nitrogen-containing heterocyclic group includes pyrrolyl, imidazolyl and pyrazole.

The hydrogen atom in a $C_{6-14}$ aryl group may be substituted by a chlorine atom, a bromine atom, an iodine atom or $C_{1-8}$ alkyl group.

The $C_{4-14}$ heteroaryl group means an aromatic heterocyclic group having one or more nitrogen atoms, oxygen atoms or sulfur atoms. The heterocyclic group is exemplified by a five-membered heteroaryl group such as pyrrolyl, imidazolyl, pyrazolyl, thienyl, furyl, oxazolyl, isooxazolyl, thiazolyl, isothiazolyl and thiadiazole; a six-membered heteroaryl group such as pyridinyl, pyrazinyl, pyrimidinyl and pyridazinyl; a condensated aromatic heterocyclic group such as indolyl, isoindolyl, quinolinyl, isoquinolinyl, benzofuranyl, isobenzofuranyl and chromenyl, preferably a $C_{4-14}$ heteroaryl group containing a nitrogen atom, and more preferably pyridinyl.

The $C_{2-24}$ alkylpolyoxyalkylene group is preferably a group represented by the formula: $-(Q^HO)_m R^H$ wherein $Q^H$ is $-CH_2-$, $-CH_2CH_2-$, $-CH_2CH_2CH_2-$, $-CH_2CH(CH_3)-$ or $-CH_2CH_2CH_2CH_2-$, $R^H$ is $-CH_3$ or $-CH_2CH_3$, m is an integer of 1 or more and 20 or less. When m is 2 or more, $Q^H$ may consist of only one type or may consist of multiple types. When $Q^H$ may consist of multiple types, the arrangement of multiple types of $Q^H$ may be random or block form.

The $C_{2-24}$ polyoxyalkylene group is preferably a group represented by the formula: $-(Q^HO)_mQ^H-$.

The $C_{2-10}$ alkylene group may be linear, branched or cyclic. The $C_{2-10}$ alkylene group is preferably a $C_{2-6}$ alkylene group, and more preferably a $C_{2-4}$ alkylene group. The $C_{2-10}$ alkylene group is preferably an ethylene group optionally substituted by one or two $C_{1-4}$ alkyl groups, more preferably an ethylene group optionally substituted by one or two $C_{1-2}$ alkyl groups, and even more preferably an ethylene group optionally substituted by one or two methyl groups, from the viewpoint that a cyclic carbonate can be easily obtained. The above-described ethylene group substituted by an alkyl group may be also described as 1,2-alkylene group.

The $C_{6-14}$ arylene group, $C_{4-14}$ heteroarylene group and $C_{2-24}$ polyoxyalkylene group are respectively divalent organic groups corresponding to a $C_{6-14}$ aryl group, a $C_{4-14}$ heteroaryl group and a $C_{2-24}$ alkylpolyoxyalkylene group.

An example of the nucleophilic functional group-containing compound (i) includes a hydroxy group-containing compound (i), a thiol group-containing compound (i) and an amino group-containing compound (i). An example of the hydroxy group-containing compound (i) includes phenol and a derivative thereof, such as phenol, 2-chlorophenol, 3-chlorophenol, 4-chlorophenol, 2-bromophenol, 3-bromophenol, 4-bromophenol, 2-methylphenol, 3-methylphenol and 4-methylphenol; a $C_{3-10}$ cycloalkanol such as cyclohexanol; benzyl alcohol and a derivative thereof, such as benzyl alcohol and 2,6-benzyl alcohol; an alkylene glycol mono($C_{1-4}$ alkyl) ether such as ethylene glycol monomethyl ether and propylene glycol monomethyl ether; an oligoalkylene glycol mono($C_{1-4}$ alkyl) ether such as diethylene glycol monomethyl ether, triethylene glycol monomethyl ether and tetraethylene glycol monomethyl ether.

An example of the thiol group-containing compound (i) includes thiophenol and a derivative thereof, such as thiophenol, 2-chlorothiophenol, 3-chlorothiophenol, 4-chlorothiophenol, 2-bromothiophenol, 3-bromothiophenol, 4-bromothiophenol, 2-methylthiophenol, 3-methylthiophenol and 4-methylthiophenol; a $C_{3-10}$ cycloalkanethiol such as cyclohexanethiol; benzyl mercaptan and a derivative thereof, such as benzyl mercaptan, 2-chlorobenzyl mercaptan, 4-chlorobenzyl mercaptan and 4-methoxybenzyl mercaptan; a 1,2-ethanedithiol mono($C_{1-4}$ alkyl) thioether such as $HSCH_2CH_2SCH_3$, $HSCH_2CH(CH_3)SCH_3$ and $HSCH(CH_3)CH_2SCH_3$; an oligo(1,2-ethanedithiol)alkylene glycol mono ($C_{1-4}$ alkyl) thioether, such as di(1,2-ethanedithiol) monomethyl thioether, tri(1,2-ethanedithiol) monomethyl thioether and tetra(1,2-ethanedithiol) monomethyl thioether.

An example of the amino group-containing compound (i) includes aniline and a derivative thereof, such as aniline, 2-chloroaniline, 3-chloroaniline, 4-chloroaniline, 2-bromoaniline, 3-bromoaniline, 4-bromoaniline, 2-methylaniline, 3-methylaniline and 4-methylaniline; a $C_{3-10}$ cycloalkylamine such as cyclohexylamine; a heterocyclic amine such as piperazine and piperidine; benzyl alcohol and a derivative thereof, such as benzylamine, 4-(aminomethyl)benzonitrile, 2-chlorobenzylamine, 3-chlorobenzylamine, 4-chlorobenzylamine, 2-bromobenzylamine, 3-bromobenzylamine, 4-bromobenzylamine and 4-t-butylbenzylamine; an alkylene glycol mono($C_{1-4}$ alkyl) ether such as N-methylethylenediamine, N,N-dimethylethylenediamine, N-methylpropylenediamine and N,N-dimethylpropylenediamine; an N-mono($C_{1-4}$ alkyl)oligoethylenediamine or an N,N-di($C_{1-4}$ alkyl)oligoethylenediamine, such as N-methyldiethylenetriamine, N,N-dimethyldiethylenetriamine, N-methyltriethylenetetramine, N,N-dimethyltriethylenetetramine, N-methyltetraethylenepentamine and N,N-dimethyltetraethylenepentamine.

Only one nucleophilic functional group-containing compound (i) may be used alone, or two or more of the nucleophilic functional group-containing compounds (i) may be used in combination. For example, when two of the nucleophilic functional group-containing compounds (i) are used, an asymmetric linear carbonate derivative can be synthesized. It is however preferred that only one nucleophilic functional group-containing compound (i) is used alone.

The nucleophilic functional group-containing compound (ii) is preferably the compounds represented by the following formulae (ii-1) and (ii-2).

wherein
A has the meaning as the above,
$R^{21}$ is a $C_{2-10}$ alkylene group, a $C_{6-14}$ arylene group or a $C_{4-14}$ heteroarylene group,
$R^{22}$ and $R^{24}$ are independently a $C_{6-14}$ arylene group or a $C_{4-14}$ heteroarylene group,
$R^{23}$ a $C_{1-10}$ alkylene group.

When the hydroxy group-containing compound (ii) is used as a starting raw material compound, the polycarbonate derivative (II-1) or the cyclic carbonate derivative (II-2) can be obtained. Specifically, when the carbon number of the main chain in $R^2$ is 2 or 3 and a stable structure such as a five-membered ring and a six-membered ring is formed with the carbonate ester group (—O—C(=O)—O—), the carbonate dithioester group (—S—C(=O)—S—) or the carbonate amide group (—NH—C(=O)—NH—), the cyclic carbonate derivative is mainly generated. In particular, when the $C_{2-10}$ alkylene group, $C_{6-14}$ arylene group and $C_{4-14}$ heteroarylene group in the nucleophilic functional group-containing compound (ii-1) are respectively a 1,2-$C_{2-10}$ alkylene group, a 1,2-$C_{6-14}$ arylene group and a 1,2-$C_{4-14}$ heteroarylene group, the cyclic carbonate is mainly generated. When the carbon number of the main chain in $R^2$ is 4 or more, a chemically more stable compound between the cyclic carbonate derivative and the polycarbonate derivative is preferentially generated depending on the reaction condition or the like.

An example of the 1,2-arylene group includes 1,2-naphthalenylene, 1,8-naphthalenylene and 2,3-naphthalenylene having the following structure in addition to 1,2-phenylene group and 1,2-biphenylene. The same is applies to 1,2-($C_{2-10}$ alkylene) group and 1,2-($C_{4-14}$ heteroarylene) group.

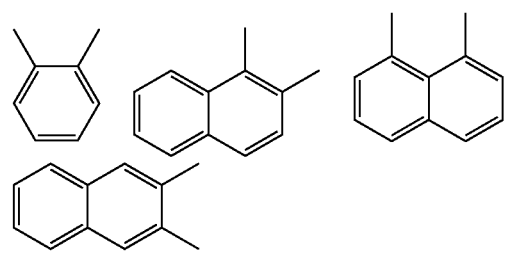

An example of the nucleophilic functional group-containing compound (ii) includes the hydroxy group-containing compound (ii), the thiol group-containing compound (ii) and the amino group-containing compound (ii). An example of the hydroxy group-containing compound (ii) includes a glycol compound such as 1,2-propanediol, 1,2-ethanediol and 1,4-butanediol; a dihydroxybenzene compound such as catechol and resorcinol; a dihydroxyheteroaryl compound such 4,6-dihydroxy-2-methylpyrimidine and 3,6-dihydroxy-4-methylpyridazine; a bisphenol compound such as Bisphenol A, Bisphenol AP, Bisphenol B, Bisphenol BP, Bisphenol E, Bisphenol F, Bisphenol TMC and Bisphenol Z.

For example, when Bisphenol A is used as the hydroxy group-containing compound (ii), the polycarbonate ester represented by the following formula is obtained.

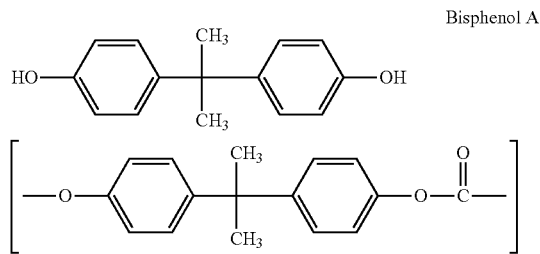

Bisphenol A

An example of the thiol group-containing compound (ii) includes a $C_{1-4}$ alkylenedithiol compound such as 1,2-propanedithiol, 1,2-ethanedithiol and 1,4-butanedithiol; a benzenedithiol compound such as 1,2-benzenedithiol and 1,3-benzenedithiol; a heteroaryldithiol compound such as 2-methylpyrimidine-4,6-dithiol and 4-methylpyridazine-3,6-dithiol; a bisthiophenol compound such as 4,4'-thiobisbenzenethiol, 2,2-bis(4-mercaptophenyl)propane, 1,1-bis(4-mercaptophenyl)-1-phenylethane, 2,2-bis(4-mercaptophenyl)butane, bis(4-mercaptophenyl)diphenylmethane, 1,1-bis(4-mercaptophenyl)ethane, bis(4-mercaptophenyl)methane, 1,1-bis(4-mercaptophenyl)-3,3,5-trimethylcyclohexane and 1,1-bis(4-mercaptophenyl)cyclohexane.

An example of the amino group-containing compound (ii) includes a $C_{1-4}$ alkylenediamine compound such as 1,2-propylenediamine, 1,3-propylenediamine, 1,2-ethylenediamine and 1,4-butylenediamine; a phenylenediamine compound such as 1,2-phenylenediamine and 1,4-phenylenediamine; a heteroaryldithiol compound such as 4,6-diamino-2-methylpyrimidine and 3,6-diamino-4-methylpyridazine; a bisaminobenzene compound such as 2,2-bis(4-aminophenyl)propane, 1,1-bis(4-aminophenyl)-1-phenylethane, 2,2-bis(4-aminophenyl)butane, bis(4-aminophenyl)diphenylmethane, 1,1-bis(4-aminophenyl)ethane, bis(4-aminophenyl)methane, 1,1-bis(4-aminophenyl)-3,3,5-trimethylcyclohexane and 1,1-bis(4-aminophenyl)cyclohexane.

Usages of the $C_{1-4}$ halogenated hydrocarbon and the nucleophilic functional group-containing compound are not particularly restricted as long as the reaction proceeds and the target product can be obtained, and for example, even when 1 time mole of the nucleophilic functional group-containing compound to the molar number of the $C_{1-4}$ halogenated hydrocarbon is used, the reaction proceeds. The molar ratio of the nucleophilic functional group-containing compound to the $C_{1-4}$ halogenated hydrocarbon, i.e. [the nucleophilic functional group-containing compound]/[the $C_{1-4}$ halogenated hydrocarbon], is preferably 0.001 or more and 1 or less in terms of the reaction efficiency and the reaction time. The molar ratio is more preferably 0.01 or more, even more preferably 0.1 or more, and more prefer- ably 0.8 or less, even more preferably 0.5 or less. When the molar ratio is excessively large, the amount of the nucleophilic functional group-containing compound proportionally becomes large and the amount of the unreacted nucleophilic functional group-containing compound is increased. On the one hand, when the molar ratio is excessively small, the amount of the unreacted $C_{1-4}$ halogenated hydrocarbon is increased and a halogenated carbonyl may be possibly leaked out of the reaction system. When the $C_{1-4}$ halogenated hydrocarbon is liquid under an ordinary temperature and an ordinary pressure and can be used as a solvent, a ratio of the nucleophilic functional group-containing compound to the $C_{1-4}$ halogenated hydrocarbon may be 1 mg/mL or more and 500 mg/mL or less.

3. Base

One or more bases selected from the group essentially consisting of a heterocyclic aromatic amine, a non-nucleophilic strong base and an inorganic base are used in the present invention method. The reaction may proceed until the polycarbonate derivative is generated by the base.

The heterocyclic aromatic amine means a compound having at least one heterocyclic ring and at least one amine functional group. An example of such a heterocyclic aromatic amine includes pyridine and a derivative thereof, such as pyridine, α-picoline, β-picoline, γ-picoline, 2,3-lutidine, 2,4-lutidine, 2,6-lutidine, 3,5-lutidine, 2-chloropyridine, 3-chloropyridine and 4-chloropyridine.

The "non-nucleophilic strong base" means a base in which a nucleophilicity of a lone pair on the nitrogen atom is weak due to a steric obstruction and of which basicity ($pK_{BH+}$) in acetonitrile is 20 or more. An example of such a non-nucleophilic strong base includes 1,5,7-triazabicyclo[4.4.0]dec-5-ene (TBD, $pK_{BH+}$: 25.98), 7-methyl-1,5,7-triazabicyclo[4.4.0]dec-5-ene (MTBD, $pK_{BH+}$: 25.44), 1,8-diazabicyclo[5.4.0]undec-7-ene (DBU, $pK_{BH+}$: 24.33), 1,5-diazabicyclo[4.3.0]non-5-ene (DBN, $pK_{BH+}$: 23.89) and 1,1,3,3-tetramethylguanidine (TMG, $pK_{BH+}$: 23.30).

An example of the inorganic base includes an alkali metal hydroxide such as lithium hydroxide, sodium hydroxide and potassium hydroxide; an alkaline earth metal hydroxide such as calcium hydroxide; an alkali metal carbonate such as sodium carbonate and potassium carbonate; an alkaline earth metal carbonate such as calcium carbonate; an alkali metal hydrogen carbonate such as sodium hydrogen carbonate.

The inorganic base may be pulverized just before use to be added to the reaction mixture, or an aqueous solution thereof is preferably added. A concentration of the inorganic base aqueous solution may be appropriately adjusted and for example, may be adjusted to 0.05 g/mL or more and 2 g/mL or less. The inorganic base aqueous solution is used for decomposing phosgene. Specifically, phosgene is decomposed into carbon dioxide and hydrogen chloride by water and the hydrogen chloride can be neutralized by an inorganic base. Since the inventor considered that the reaction of the present invention proceeds via phosgene, what is remarkable is that the present invention reaction proceeds even when an inorganic base aqueous solution is used as Example described later. In addition, since the present invention reaction proceeds even when an inorganic base aqueous solution is used, the reaction may possibly proceed without going through phosgene.

One base may be used alone, or two or more of the bases may be used in combination.

A usage of the base may be appropriately adjusted as long as the reaction successfully proceeds, and for example, a ratio to the nucleophilic functional group-containing compound may be adjusted to 1.5 times or more by mole and 10 times or less by mole. When the usage of the base is larger, the yield generally becomes larger; therefore, the ratio is preferably 2.0 times or more by mole, more preferably 3.0 times or more by mole, and even more preferably 4.0 times or more by mole.

4. Reaction Condition

The present invention method comprises the step to irradiate light on a composition containing the $C_{1-4}$ halogenated hydrocarbon, nucleophilic functional group-containing compound and base in the presence of oxygen.

A manner to mix the $C_{1-4}$ halogenated hydrocarbon, nucleophilic functional group-containing compound and base is not particularly restricted. For example, total amount of each compound may be preliminarily mixed in a reaction vessel, the compounds may be added in several portions or continuously added at any speed. When one of or both of the $C_{1-4}$ halogenated hydrocarbon and nucleophilic functional group-containing compound are not liquid in an ordinary temperature and an ordinary pressure, a solvent which can appropriately dissolve the raw material compounds and which does not inhibit the present invention reaction may be used. An example of such a solvent includes an aliphatic hydrocarbon solvent such as n-hexane; an aromatic hydrocarbon solvent such as benzene, toluene, xylene and chlorobenzene; an ether solvent such as diethyl ether, tetrahydrofuran and dioxane; and a nitrile solvent such as acetonitrile.

An oxygen source may be a gas containing oxygen, and for example, air or purified oxygen may be used. Purified oxygen may be mixed with an inert gas such as nitrogen and argon to be used. It is preferred to use air in terms of cost and easiness. An oxygen content in the air used as an oxygen source is preferably about 15 vol % or more and about 100 vol % or less in terms of high decomposition efficiency of the $C_{1-4}$ halogenated hydrocarbon by light irradiation. The oxygen content may be appropriately determined depending on the kind of the $C_{1-4}$ halogenated hydrocarbon or the like. For example, when a $C_{1-4}$ chlorohydrocarbon compound such as dichloromethane, chloroform and tetrachloroethylene is used as the $C_{1-4}$ halogenated hydrocarbon, the oxygen content is preferably 15 vol % or more and 100 vol % or less. When a $C_{1-4}$ bromohydrocarbon compound such as dibromomethane and bromoform is used, the oxygen content is preferably 90 vol % or more and 100 vol % or less. Even when oxygen is used or the oxygen content is 100 vol %, the oxygen content can be controlled in the above-described range by adjusting a flow rate of oxygen into the reaction system. A manner to supply a gas containing oxygen is not particularly restricted, and the gas may be supplied into the reaction system from an oxygen tank equipped with a flow rate adjustor or from an oxygen generating device.

The term "in the presence of oxygen" means any one of the state that the above-described each compound is contacted with oxygen and the state that there is oxygen in the above-described composition. The reaction of the present invention may be carried out under a stream of a gas containing oxygen but it is preferred to supply a gas containing oxygen into the composition by bubbling in terms of a high yield of the product.

An amount of oxygen-containing gas may be appropriately determined depending on the amount of the $C_{1-4}$ halogenated hydrocarbon or a shape of a reaction vessel. For example, an amount of the gas supplied to a reaction vessel per 1 minute to the $C_{1-4}$ halogenated hydrocarbon in the reaction vessel is preferably 5 times or more by volume. The ratio is more preferably 25 times or more by volume, and even more preferably 50 times or more by volume. The upper limit of the ratio is not particularly restricted, and the ratio is preferably 500 times or less by volume, more preferably 250 times or less by volume, and even more preferably 150 times or less by volume. The amount of oxygen supplied to a reaction vessel per 1 minute to the $C_{1-4}$ hydrocarbon compound in the reaction vessel may be 5 times or more by volume and 25 times or less by volume. When an amount of the gas is excessively large, the $C_{1-4}$ hydrocarbon compound may be possibly volatilized, but when the amount is excessively small, it may possibly become difficult to develop the reaction.

The light irradiated on the composition is preferably a light containing a short wavelength light, more preferably a light containing ultraviolet light, and preferably a light containing a light having a wavelength of 180 nm or more and 500 nm or less specifically. A wavelength of the light may be appropriately determined depending on the kind of the $C_{1-4}$ halogenated hydrocarbon, and is more preferably 400 nm or less and even more preferably 300 nm or less. When the irradiated light contains a light of the above-described wavelength range, the $C_{1-4}$ halogenated hydrocarbon undergoes oxidative photodecomposition in an efficient fashion.

A means for the light irradiation is not particularly restricted as long as the light of the above-described wavelength can be irradiated by the means. An example of a light source of the light having such a wavelength range includes sunlight, low pressure mercury lamp, medium pressure mercury lamp, high pressure mercury lamp, ultrahigh pressure mercury lamp, chemical lamp, black light lamp, metal halide lamp and LED lamp. A low pressure mercury lamp is preferably used in terms of a reaction efficiency and a cost.

The conditions such as a strength of the irradiated light, an irradiation time or the like may be appropriately determined depending on the kind and usage amount of the raw material compounds, and for example, a strength of the irradiated light is preferably 10 $\mu W/cm^2$ or more and 500 $\mu W/cm^2$ or less. The irradiated light strength is more preferably 100 $\mu W/cm^2$ or less, and even more preferably 40 $\mu W/cm^2$ or less. An irradiation time is preferably 0.5 hours or more and 10 hours or less, more preferably 1 hour or more and 6 hours or less, and even more preferably 2 hours or more and 4 hours or less. A manner to irradiate the light is not also particularly restricted, and any manners can be selected. For example, the light may be continuously irradiated from the reaction initiation to the reaction completion, irradiation and unirradiation of the light may be alternately repeated, and the light may be irradiated from the reaction initiation for a predetermined time only. It is preferred to continuously irradiate the light from the reaction initiation to the reaction completion.

A temperature during the reaction is not particularly restricted and may be appropriately adjusted, and for example, may be adjusted to 0° C. or higher and 50° C. or lower. The temperature is more preferably 10° C. or higher, even more preferably 20° C. or higher, and more preferably 40° C. or lower, even more preferably 30° C. or lower.

A reaction apparatus usable in the production method of the present invention is exemplified by a reaction vessel equipped with a light irradiation means. A reaction apparatus may be equipped with a stirring device and a temperature control means. One embodiment of a reaction apparatus usable in the production method of the present invention is shown as FIG. 1. The reaction apparatus shown as FIG. 1 has a light irradiation means 1 in a tubular reaction vessel 6. The above-described raw material compounds are added into a tubular reaction vessel 6, and a light is irradiated by using a light irradiation means 1 while a gas containing oxygen is supplied into the tubular reaction vessel 6 or a gas containing oxygen is blown into the composition to cause bubbling (not shown in the FIGURE) for the reaction. When a light irradiation means 1 is covered with a jacket 2 or the like, it is preferred that the jacket is composed of a material through which the short wavelength light penetrates. A light may be irradiated from outside a reaction vessel. In such a case, the reaction vessel is composed of a material through which the short wavelength light penetrates. A material through which the short wavelength light penetrates is not particularly restricted as long as the effect of the present invention is not inhibited, and is preferably exemplified by quartz glass.

The product obtained by the reaction may be purified by a conventionally known method. An example of such a purification method includes distillation, removal of raw material compounds under reduced pressure, column chromatography, liquid separation, extraction, washing and recrystallization.

When the hydroxy group-containing compound, thiol group-containing compound or amino group-containing compound is used as the raw material nucleophilic functional group-containing compound, a carbonate derivative respectively having a carbonate ester group (—O—C(=O)—O—), a carbonate dithioester group (—S—C(=O)—S—) or a urea group (—NH—C(=O)—NH—) is obtained. When the hydroxy group-containing compound and amino group-containing compound are used in combination, a carbonate derivative having a urethane group (—O—C(=O)—NH—) is obtained. When the thiol group-containing compound and amino group-containing compound are used in combination, a carbonate derivative having a thiourethane group (—S—C(=O)—NH—) is obtained.

The linear carbonate derivative (I) produced by the present invention method is useful as a non-aqueous solvent or the like. For example, the linear carbonate (I) can be used as an electrolyte solvent of a lithium-ion secondary battery. The polycarbonate (II) is useful as an excellent engineering plastic.

The present application claims the benefit of the priority date of Japanese patent application No. 2017-97681 filed on May 16, 2017. All of the contents of the Japanese patent application No. 2017-97681 filed on May 16, 2017, are incorporated by reference herein.

EXAMPLES

Hereinafter, the present invention is described in more detail with Examples. The present invention is however not restricted to the following Examples in any way, and it is possible to work the present invention according to the Examples with an additional appropriate change within the range of the above descriptions and the following descriptions. Such a changed embodiment is also included in the technical scope of the present invention.

Comparative Example 1: Synthesis of Dimethyl Carbonate

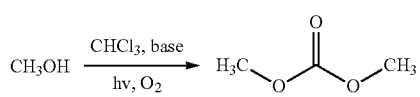

A quartz glass jacket having a diameter of 30 mm was inserted into a tubular reaction vessel having a diameter of 42 mm and a volume of 100 mL, and a low pressure mercury lamp ("UVL20PH-6" manufactured by SEN Light, 20 W, φ24×120 mm) was further inserted into the quartz glass jacket to construct a reaction system. A schematic picture of the reaction system is shown in FIG. 1. In the reaction vessel, purified chloroform (20 mL), methanol (0.405 mL, 10 mmol) and 5 times by mole of pyridine (4.03 mL) to the methanol were added. The mixture was stirred to be mixed. Oxygen gas was blown into the stirred reaction mixture at a flow rate of 0.5 L/min at 20° C. to cause bubbling, and a light was irradiated from the low pressure mercury lamp. The reaction mixture was analyzed by $^1$H-NMR after 3 hours; as a result, it was confirmed that the yield of dimethyl carbonate as the target compound was slightly 1.6%.

Comparative Example 2

The reaction was carried out similarly to the above-described Comparative example 1 except that ethanol was used instead of methanol. It was not confirmed that the reaction proceeded even after 3 hours. With consideration given to the result together with the result of Comparative Example 1, it became clear that the present invention method is difficult to be applied to a monovalent alcohol.

Example 1: Synthesis of Diphenyl Carbonate

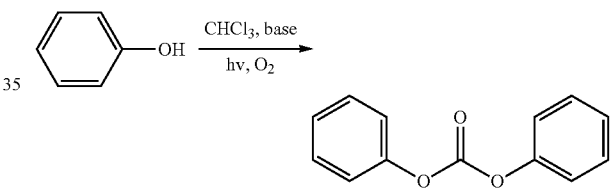

(1) Use of Pyridine as Base

The reaction was carried out similarly to the above-described Comparative example 1 except that phenol (0.94 g, 10 mmol) was used instead of methanol, the usage amount of pyridine was adjusted to 3.5 times by mole to phenol, and the reaction time was 2 hours. After the reaction, water and dichloromethane were added to the reaction mixture, and an organic phase and a water phase were separated. The organic phase was dried by anhydrous sodium sulfate, and then the solvent was distilled away under reduced pressure. The thus obtained solid was recrystallized by using dichloromethane and n-hexane to obtain diphenyl carbonate as white solid target compound (isolation yield: 61%).

(2) Use of Pyridine as Base

Diphenyl carbonate as white solid target compound was obtained (isolation yield: more than 99%) similarly to the above-described Example 1(1) except that 5 times by mole of pyridine to phenol was used and the reaction time was 1 hour.

(3) Use of 2,6-Lutidine as Base

Diphenyl carbonate as the target compound was obtained (isolation yield: 60%) similarly to the above-described Example 1(1) except that 2,6-lutidine was used instead of pyridine and the reaction time was 1 hour.

(4) Use of Carbon Tetrachloride

The reaction was carried out similarly to the above-described Example 1(1) except that carbon tetrachloride (25 mL) was used instead of chloroform, and 5 times by mole of pyridine to phenol was used. After the reaction, water and dichloromethane were added to the reaction mixture, and an organic phase and a water phase were separated. The organic phase was dried by anhydrous sodium sulfate, and then the solvent was distilled away under reduced pressure. The thus obtained solid was recrystallized by using dichloromethane and n-hexane to obtain diphenyl carbonate as white solid target compound (isolation yield: 69%).

Comparative Example 3

The reaction was carried out similarly to the above-described Example 1(2) except that triethylamine was used instead of pyridine. But only a slight amount of a black tarry substance was isolated and diphenyl carbonate as the target compound could not be isolated. As just described, when triethylamine was used as an organic base, diphenyl carbonate could not be obtained; on the one hand, diphenyl carbonate could be obtained with a yield of more than 99% by only changing an organic base from triethylamine to pyridine.

Example 2: Synthesis of Bis(Pentachlorophenyl) Carbonate

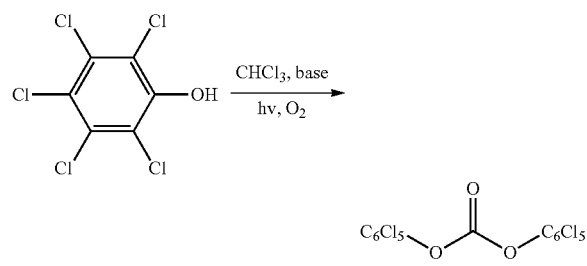

The reaction was carried out similarly to the above-described Comparative example 1 except that pentachlorophenol (1.13 g, 5 mmol) was used instead of methanol. After the reaction, methanol was added to the suspended reaction mixture to generate a white solid. The generated white solid was obtained by suction filtration as the target compound bis(pentachlorophenyl) carbonate (isolation yield: 72%).

Example 3: Synthesis 1,3-Benzodioxole-2-One

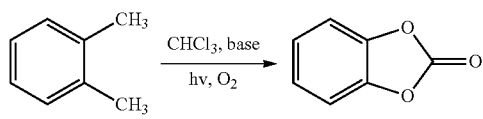

Purified chloroform (20 mL), catechol (1.1 g, 10 mmol) and 5 times by mole of pyridine (4.03 mL) to the catechol were added to the above-described reaction vessel, and the mixture was stirred to be mixed. Oxygen gas was blown into the stirred reaction mixture at a flow rate of 0.5 L/min at 20° C. to cause bubbling, and a light was irradiated from the low pressure mercury lamp. After 2 hours, water and dichloromethane were added to the reaction mixture, and an organic phase and a water phase were separated. The organic phase was dried by anhydrous sodium sulfate, and then the solvent was distilled away under reduced pressure. The thus obtained solid was recrystallized by using dichloromethane and n-hexane to obtain the target 1,3-benzodioxole-2-one (isolation yield: more than 99%).

Example 4: Synthesis of Ethylene Carbonate

The reaction was carried out similarly to the above-described Example 3 except that ethylene glycol (0.28 mL, 10 mmol) was used instead of catechol. After the reaction, the reaction mixture was analyzed by $^1$H-NMR to confirm that the target ethylene carbonate was generated (isolation yield: 44%).

Example 5: Synthesis of Bisphenol A Polycarbonate

Purified chloroform (20 mL), Bisphenol A (2.28 g, 10 mmol) and 5 times by mole of pyridine (4.03 mL) to the Bisphenol A were added to the above-described reaction vessel, and the mixture was stirred to be mixed. Oxygen gas was blown into the stirred reaction mixture at a flow rate of 0.5 L/min at 20° C. to cause bubbling, and a light was irradiated from the low pressure mercury lamp. Since the stirring bar could not rotated due to increased viscosity of the reaction mixture after 40 minutes, methanol (30 mL) was added to the reaction mixture, ultrasonic waves were irradiated, and the reaction mixture was filtrated by suction. The obtained solid was washed with methanol and then dried in vacuo to obtain a white solid. The white solid was analyzed by $^1$H-NMR; as a result, it was confirmed that the target Bisphenol A polycarbonate could be generated with a yield of more than 99%.

The obtained Bisphenol A polycarbonate was analyzed by gel permeation chromatography (GPC) in the following condition to determine the molecular weight. The result is shown in Table 1.

Device: High Performance GPC Device ("HLC-8320GPC" manufactured by Tosoh Corporation)
Column: Column for Super High Molecular ("TSKgel GMHHR-Hx2" manufactured by Tosoh Corporation)

| | |
|---|---|
| Moving phase: chloroform | Flow rate: 1.0 mL/min |
| Oven temperature: 40° C. | Concentration: 0.3 w/v % |
| Injected amount: 100 μL | |
| Molecular weight standard: polystyrene | |
| Detector: RI | |

TABLE 1

| Mn | Mw | Mw/Mn |
|---|---|---|
| 23,000 | 52,000 | 2.3 |

As the result shown in Table 1, it was found that the polycarbonate ester synthesized by the present invention method has sufficiently high molecular weight, and the molecular weight distribution is relatively narrow.

Example 6: Synthesis of Bis(Triethylene Glycol Monomethyl Ether) Carbonate

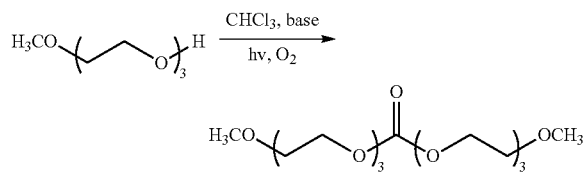

The reaction was carried out similarly to the above-described Comparative example 1 except that triethylene glycol monomethyl ether (1.64 g, 10 mmol) was used instead of methanol. After the reaction, water and a mixed solvent of dichloromethane:ethyl acetate=1:1 were added to the reaction mixture, and an organic phase and a water phase were separated. The organic phase was dried by anhydrous sodium sulfate, and then concentrated under reduced pressure to obtain bis(triethylene glycol monomethyl ether) carbonate as the brown oily target compound (isolation yield: more than 99%).

Example 7: Synthesis of Tetraethylene Glycol Polycarbonate

The reaction was carried out similarly to the above-described Comparative example 1 except that tetraethylene glycol (1.50 g, 10 mmol) was used instead of methanol and the reaction time was 2 hours. After the reaction, water and ethyl acetate were added to the reaction mixture, and an organic phase and a water phase were separated. The organic phase was washed three times with salt water. The organic phase was dried by anhydrous sodium sulfate and then concentarated under reduced pressure to obtain tetraethylene glycol polycarbonate as the brown oily target compound (isolation yield: more than 99%).

$^1$H-NMR (400 MHz, CDCl$_3$) δ4.28 (t, J=4.8 Hz, —CO$_2$CH$_2$—), 3.73 (t, J=4.8 Hz, —CH$_2$—), 3.68-3.63 (m, —CH$_2$—);

FAB-MS: m/z 519, 739, 958;

IR (KBr): 2955, 2891, 1740, 1459, 1396, 1354, 1271, 1100, 1029, 950, 864, 791 cm$^{-1}$

Example 8: Photoinduced Copolymerization of Bisphenol a and Hexamethylenediamine

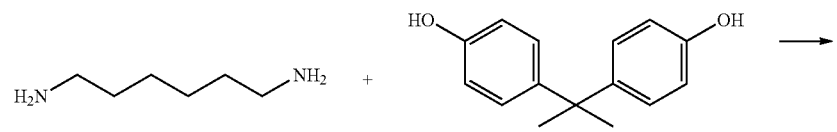

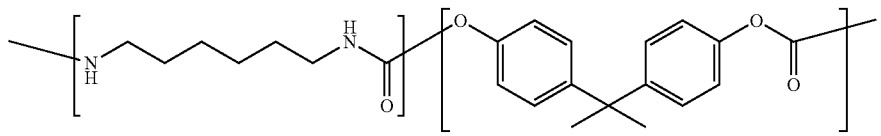

Purified chloroform (30 mL), Bisphenol A (0.685 g, 3 mmol), hexamethylenediamine (0.412 g, 3 mmol), and sodium hydroxide aqueous solution (20 mL, 100 mmol) were added to the above-described reaction vessel, and the mixture was stirred to be mixed. Oxygen gas was blown into the stirred reaction mixture at a flow rate of 0.5 L/min at 20° C. to cause bubbling, and a light was irradiated from the low pressure mercury lamp. After 2 hours, water and dichloromethane were added to the reaction mixture. The generated precipitate was obtained by filtration, washed with methanol, and dried in vacuo at 70° C. An organic phase and a water phase of the filtrate were separated. The organic phase was concentrated under reduced pressure. The thus obtained residue was washed with methanol and then dried in vacuo at 70° C. to obtain a light orange powder (yield: 39%). The obtained powder was analyzed by ¹H-NMR and IR; as a result, it was confirmed that the target copolymer was generated.

As described above, even when an aqueous solution of an inorganic base was used, a carbonate derivative could be produced. Since an inorganic base aqueous solution is used for decomposing phosgene, the above-described experimental result is not expected by any means and it is considered that the reaction according to the present invention may possibly proceed without passing through phosgene.

Since the firstly obtained precipitate was insoluble in a solvent and the powder obtained from the filtrate was soluble in DMSO or the like, the molecular weights of the both powders may be different.

Example 9: Synthesis of Bisphenyl Carbonate

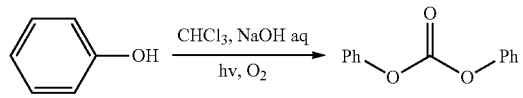 [SMILES: Oc1ccccc1 ; O=C(Oc1ccccc1)Oc1ccccc1]

Purified chloroform (20 mL), phenol (0.941 g, 10 mmol) and sodium hydroxide aqueous solution (20 mL, 100 mmol) were added to the above-described reaction vessel, and the mixture was stirred to be mixed. Oxygen gas was blown into the stirred reaction mixture at a flow rate of 0.5 L/min at 20° C. to cause bubbling, and a light was irradiated from the low pressure mercury lamp. After 3 hours, water and dichloromethane were added to the reaction mixture. An organic phase and a water phase were separated. The organic phase was dried by anhydrous sodium sulfate and then concentrated under reduced pressure at 70° C. to obtain a light orange solid (yield: 55%). The obtained solid was analyzed by ¹H-NMR; as a result, it was confirmed that the target compound was generated.

Example 10: Synthesis of Dicyclohexyl Carbonate

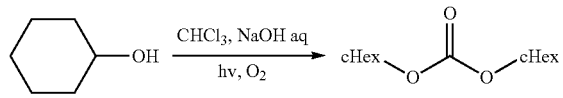

A light yellow liquid was obtained (yield: 13%) similarly to the above-described Example 9 except that cyclohexanol (1.06 mL, 10 mmol) was used instead of phenol. The obtained liquid was analyzed by ¹H-NMR; as a result, it was confirmed that the target compound was generated.

Example 11: Synthesis of Bis(4-t-Butylphenyl) Carbonate

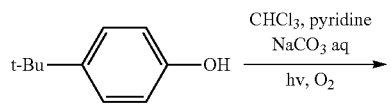

-continued

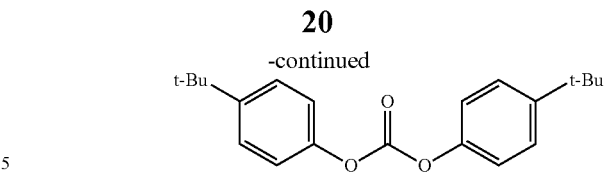

Purified chloroform (20 mL), 4-t-butylphenol (1.53 g, 10 mmol), sodium carbonate aqueous solution (20 mL, 50 mmol) and pyridine (0.202 mL, 5 mmol) were added to the above-described reaction vessel, and the mixture was stirred to be mixed. Oxygen gas was blown into the stirred reaction mixture at a flow rate of 0.5 L/min at 20° C. to cause bubbling, and a light was irradiated from the low pressure mercury lamp. After 3 hours, chloroform and water were added to the reaction mixture, and an organic phase and a water phase were separated. The organic phase was dried by anhydrous sodium sulfate and then concentrated under reduced pressure at 70° C. The thus obtained residue was recrystallized to obtain a light orange powder (yield: 57.0%). The obtained powder was analyzed by ¹H-NMR; as a result, it was confirmed that the target compound was generated.

Example 12: Synthesis of Bis(4-Methoxyphenyl) Carbonate

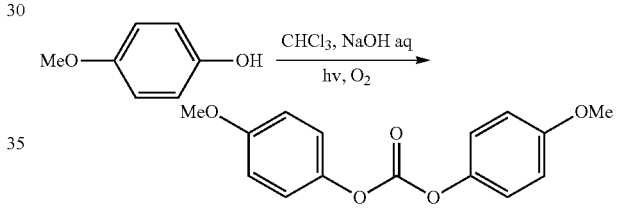

A brown solid was obtained (yield: 60%) similarly to the above-described Example 9 except that 4-methoxyphenol (10 mmol) was used instead of phenol and 30 mL of chloroform was used. The obtained solid was analyzed by ¹H-NMR and IR; as a result, it was confirmed that the target compound was generated.

Example 13: Synthesis of Bis(4-Nitrophenyl) Carbonate

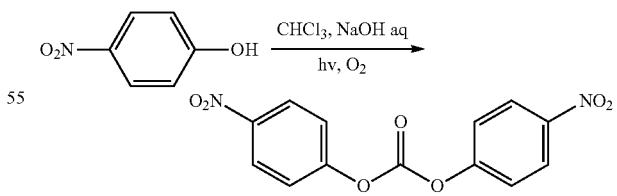

A white powder was obtained (yield: 5%) similarly to the above-described Example 9 except that 4-nitrophenol (1.391 g, 10 mmol) was used instead of phenol, 30 mL of chloroform was used, and the reaction time was 2 hours. The obtained powder was analyzed by ¹H-NMR and IR; as a result, it was confirmed that the target compound was generated.

Example 14: Synthesis of Bisphenol A Polycarbonate

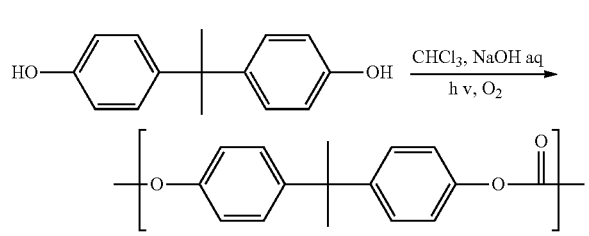

Purified chloroform (20 mL), Bisphenol A (1.14 g, 5 mmol), and sodium hydroxide aqueous solution (100 mmol, 20 mL) were added to the above-described reaction vessel, and the mixture was stirred to be mixed. Oxygen gas was blown into the stirred reaction mixture at a flow rate of 0.5 L/min at 20° C. to cause bubbling, and a light was irradiated from the low pressure mercury lamp. After 2 hours, an organic phase and a water phase were separated. The organic phase was dried by anhydrous sodium sulfate and then concentrated under reduced pressure. After chloroform and methanol were added thereto and the solvent was removed by decantation, the residue was dried at 70° C. under reduced pressure to obtain a white solid (yield: 79%). The obtained solid was analyzed by $^1$H-NMR; as a result, it was confirmed that the target compound was generated.

The molecular weight of the obtained Bisphenol A polycarbonate was determined in a similar condition to the above-described Example 5. The result is shown in Table 2.

TABLE 2

| Mn | Mw | Mw/Mn |
|---|---|---|
| 4,600 | 15,200 | 3.3 |

As the result shown in Table 2, it was found that the polycarbonate ester synthesized by the present invention method has sufficiently high molecular weight, and the molecular weight distribution is relatively narrow.

Example 15: Synthesis of Dihexyl Carbonate

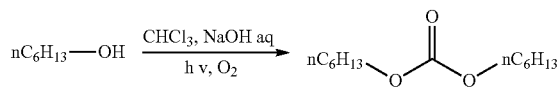

The reaction was carried out similarly to the above-described Example 9 except that 1-hexanol (1.25 mL, 10 mmol) was used instead of phenol. The reaction mixture was dried by anhydrous sodium sulfate. Dichloromethane (0.64 mL, 10 mmol) was added thereto as an internal standard, and the reaction mixture was directly analyzed by $^1$H-NMR; as a result, it was confirmed that the target compound was generated (yield: >99%).

Example 16: Synthesis of Dipentyl Carbonate

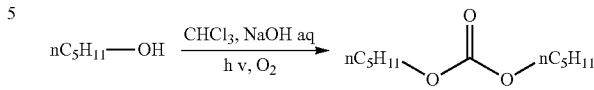

The reaction was carried out similarly to the above-described Example 9 except that 1-pentanol (10 mmol) was used instead of phenol. The reaction mixture was dried by anhydrous sodium sulfate. Dichloromethane (0.64 mL, 10 mmol) was added thereto as an internal standard, and the reaction mixture was directly analyzed by $^1$H-NMR; as a result, it was confirmed that the target compound was generated (yield: 12%).

Example 17: Synthesis of 1,3-Diphenylurea

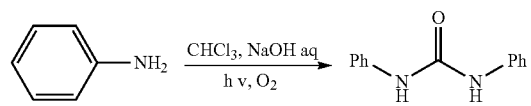

Purified chloroform (20 mL), aniline (0.93 g, 10 mmol) and sodium hydroxide aqueous solution (NaOH: 4 g, 20 mL) were added to the above-described reaction vessel, and the mixture was stirred to be mixed. Oxygen gas was blown into the stirred reaction mixture at a flow rate of 0.5 L/min at 20° C. to cause bubbling, and a light was irradiated from the low pressure mercury lamp. After 2 hours, dichloromethane and water were added to the reaction mixture, and an organic phase and a water phase were separated. The organic phase was dried by anhydrous sodium sulfate and then concentrated under reduced pressure. The thus obtained black solid was recrystallized by using dichloromethane and n-hexane to obtain black powder (yield amount: 0.13 g, yield: 12%). The obtained solid was analyzed by $^1$H-NMR; as a result, it was confirmed that the target compound was generated.

Example 18: Synthesis of 1,3-Dicyclohexylurea

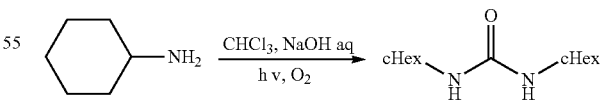

A white powder was obtained (yield amount: 0.69 g, yield: 62%) similarly to the above-described Example 17 except that cyclohexylamine (1.17 mL, 10 mmol) was used instead of aniline, the reaction time was 3 hours, and after the reaction, the precipitate generated by adding hexane and water was obtained by filtration and dried in vacuo. The obtained powder was analyzed by $^1$H-NMR; as a result, it was confirmed that the target compound was generated.

Example 19: Synthesis of 1,3-Dibenzylurea

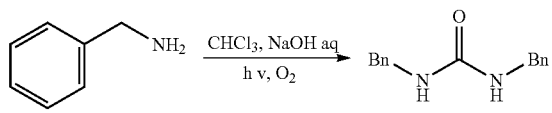 [SMILES: NCc1ccccc1 ; O=C(NCc1ccccc1)NCc1ccccc1]

A light brown powder as the target compound was obtained (yield amount: 0.78 g, yield: 65%) similarly to the above-described Example 17 except that benzylamine (1.07 g, 10 mmol) was used instead of aniline, the reaction time was 5 hours, and hexane and water was added to the reaction mixture after the reaction to obtain a precipitate by filtration and the precipitate was dried in vacuo. The obtained powder was analyzed by $^1$H-NMR; as a result, it was confirmed that the target compound was generated.

Example 20: Synthesis of 1,3-Dihexylurea

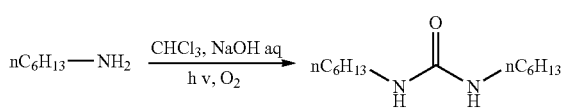

A white powder was obtained (yield amount: 0.58 g, yield: 51%) similarly to the above-described Example 17 except that 1-hexylamine (1.01 g, 10 mmol) was used instead of aniline, the reaction temperature was 10° C., and the reaction time was 3 hours. The obtained powder was analyzed by $^1$H-NMR; as a result, it was confirmed that the target compound was generated.

Example 21: Synthesis of 1,3-Dihexylurea

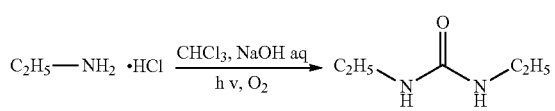

A yellow crystal was obtained (yield amount: 0.08 g, yield: 14%) similarly to the above-described Example 17 except that ethylamine hydrochloride (0.82 g, 10 mmol) was used instead of aniline, the reaction temperature was 10° C., the reaction time was 5 hours, and ethyl acetate was used after the reaction instead of dichloromethane. The obtained crystal was analyzed by $^1$H-NMR; as a result, it was confirmed that the target compound was generated.

Example 22: Synthesis of 1,3-Dipiperidinylurea

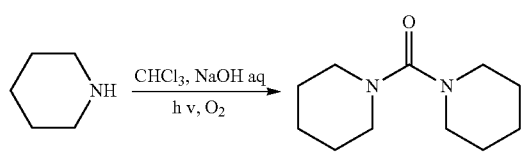 [SMILES: C1CCNCC1 ; O=C(N1CCCCC1)N1CCCCC1]

A yellow crystal was obtained (yield amount: 0.38 g, yield: 38%) similarly to the above-described Example 17 except that piperidine (0.85 g, 10 mmol) was used instead of aniline, the reaction time was 3 hours, and the target compound was purified by using a short silica gel column (eluent: dichloromethane). The obtained crystal was analyzed by $^1$H-NMR; as a result, it was confirmed that the target compound was generated.

Example 23: Photoinduced Copolymerization of Bisphenol a and Hexamethylenediamine The reaction was carried out at 20° C. for 2 hours similarly to the above-described Example 8 except that diazabicycloundecene (60 mmol) was used instead of sodium hydroxide aqueous solution. Then, the reaction was further carried out at 50° C. for 15 minutes. After the reaction, water was added and the reaction mixture was left to stand overnight. Then, an organic phase and an aqueous phase were separated. The organic phase was dried by anhydrous sodium sulfate and then concentrated under reduced pressure. The residue was washed with hexane and dried at 70° C. under reduced pressure. After the residue was further washed with dichloromethane and hexane, the residue was dried under reduced pressure to obtain a light orange powder (yield: >99%). The obtained powder was analyzed by $^1$H-NMR and IR; as a result, it was confirmed that the target copolymer was generated.

Example 24: Synthesis of 1,3-Diphenylurea

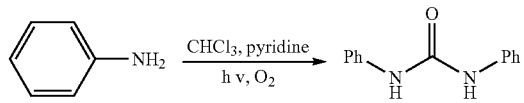

Purified chloroform (20 mL), aniline (0.93 g, 10 mmol) and pyridine (4.01 mL, 50 mmol) were added to the above-described reaction vessel, and the mixture was stirred to be mixed. Oxygen gas was blown into the stirred reaction mixture at a flow rate of 0.5 L/min at 20° C. to cause bubbling, and a light was irradiated from the low pressure mercury lamp. After 2 hours, dichloromethane and water were added to the reaction mixture, and an organic phase and a water phase were separated. The organic phase was dried by anhydrous sodium sulfate and then concentrated under reduced pressure. The thus obtained residue was dissolved in dichloromethane and ethyl acetate, and aniline black was removed by passing the solution through an alumina column. The liquid treated by the column was concentrated under reduced pressure, and the residue was recrystallized by using ethyl acetate and hexane to obtain a light brown needle crystal (yield amount: 0.54 g, yield: 51%). The obtained crystal was analyzed by $^1$H-NMR; as a result, it was confirmed that the target compound was generated.

Example 25: Synthesis of 1,3-Diphenylurea

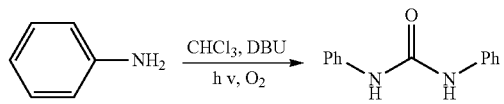

The reaction was carried out at 20° C. for 2 hours similarly to the above-described Example 24 except that diazabicycloundecene (7.48 mL, 50 mmol) was used instead of pyridine. After the reaction, dichloromethane and water were added to the reaction mixture, and an organic phase and an aqueous phase were separated. The organic phase was dried by anhydrous sodium sulfate and then concentrated under reduced pressure. The thus obtained residue was dissolved in THF, and an impurity was removed by passing the solution through an alumina column. The liquid treated by the column was concentrated under reduced pressure, and the residue was recrystallized by dichloromethane and hexane to obtain a light orange crystal (yield amount: 0.44 g, yield: 38%).

Example 26: Synthesis of 1,3-Dicyclohexylurea

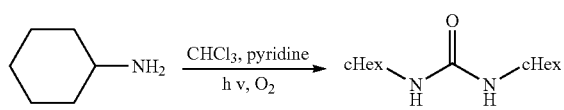

The reaction was carried out at 20° C. for 4 hours similarly to the above-described Example 24 except that cyclohexylamine (1.17 mL, 10 mmol) was used instead of aniline. After the reaction, dichloromethane and water were added, and an organic phase and an aqueous phase were separated. The organic phase was dried by anhydrous sodium sulfate and then concentrated under reduced pressure. The residue was recrystallized by dichloromethane and hexane to obtain a light brown crystal (yield amount: 0.16 g, yield: 14%). The obtained crystal was analyzed by $^1$H-NMR; as a result, it was confirmed that the target compound was generated.

Example 27: Synthesis of Polyurea

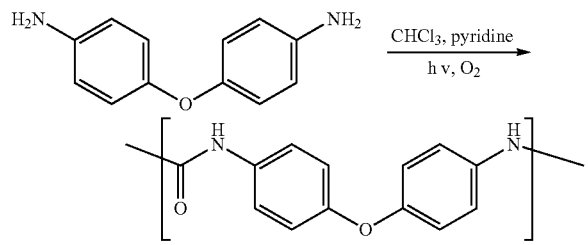

Purified chloroform (20 mL), 4,4'-diaminodiphenyl ether (0.50 g, 2.5 mmol) and pyridine (1.0 mL, 12.5 mmol) were added to the above-described reaction vessel, and the mixture was stirred to be mixed. Oxygen gas was blown into the stirred reaction mixture at a flow rate of 0.5 L/min at 20° C. to cause bubbling, and a light was irradiated from the low pressure mercury lamp. After 1.5 hours, dichloromethane and water were added to the reaction mixture, and an organic phase and a water phase were separated. The organic phase was dried by anhydrous sodium sulfate and then concentrated under reduced pressure. The thus obtained residue was washed with methanol to obtain a brown powder (yield amount: 0.14 g, yield: 25%). The obtained crystal was analyzed by $^1$H-NMR and IR; as a result, it was confirmed that the target compound was generated.

Example 28: Synthesis of Carbonyldiimidazole

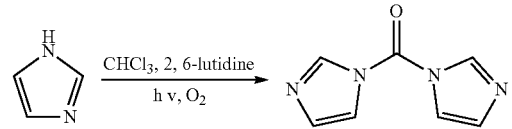 [SMILES: c1c[nH]cn1 ; O=C(n1ccnc1)n1ccnc1]

Purified chloroform (20 mL), imidazole (0.68 g, 10 mmol) and 2,6-lutidine (5.79 mL, 50 mmol) were added to the above-described reaction vessel, and the mixture was stirred to be mixed. Oxygen gas was blown into the stirred reaction mixture at a flow rate of 0.5 L/min at 20° C. to cause bubbling, and a light was irradiated from the low pressure mercury lamp. After the irradiation was stopped, the reaction was carried out at 50° C. for 30 minutes. Dichloromethane (5 mmol) was added to the reaction mixture as an internal standard and the reaction mixture was analyzed by $^1$H-NMR; as a result, it was confirmed that the target compound was generated with a yield of 38%.

Example 29: Synthesis of S,S'-Diphenyl Dithiocarbonate

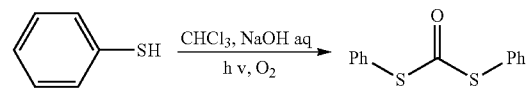 [SMILES: Sc1ccccc1 ; O=C(Sc1ccccc1)Sc1ccccc1]

Purified chloroform (20 mL), thiophenol (1.03 mL, 10 mmol) and sodium hydroxide aqueous solution (NaOH: 4 g, 20 mmol) were added to the above-described reaction vessel, and the mixture was stirred to be mixed. Oxygen gas was blown into the stirred reaction mixture at a flow rate of 0.5 L/min to cause bubbling, and a light was irradiated from the low pressure mercury lamp to carry out the reaction at 20° C. for 2 hours. Then, dichloromethane and water were added to the reaction mixture, and an organic phase and a water phase were separated. The organic phase was dried by anhydrous sodium sulfate and then concentrated under reduced pressure to obtain a brown liquid. The obtained brown liquid was analyzed by $^1$H-NMR; as a result, it was confirmed that the target compound was generated with a yield of 20%.

EXPLANATION OF REFERENCES

1: Light-irradiating means, 2: Jacket, 3: Water bath, 4: Stirring bar, 5: Heating medium or Cooling medium, 6: Tubular reaction vessel

The invention claimed is:
1. A method for producing a carbonate derivative, comprising
irradiating a light on a composition containing a $C_{1-4}$ halogenated hydrocarbon having one or more halogen atoms selected from the group consisting of a chlorine atom, a bromine atom and an iodine atom, a nucleophilic functional group-containing compound and a base in the presence of oxygen,
wherein the nucleophilic functional group-containing compound is represented by the following formula (i) and the carbonate derivative is a linear carbonate derivative represented by the following formula (I), or the nucleophilic functional group-containing compound is represented by the following formula (ii), Bisphenol A, Bisphenol AP, Bisphenol B, Bisphenol BP, Bisphenol TMC or Bisphenol Z, and the carbonate derivative is a polycarbonate derivative containing a unit represented by the following formula (II-1), a polycarbonate ester of Bisphenol A, Bisphenol AP, Bisphenol B, Bisphenol BP, Bisphenol TMC or Bisphenol Z, or a cyclic carbonate derivative represented by the following formula (II-2):

$$R^1-A-H \quad (i)$$
$$H-A-R^2-A-H \quad (ii)$$
$$R^1-A-C(=O)-A-R^1 \quad (I)$$
$$[-A-R^2-A-C(=O)-] \quad (II-1)$$

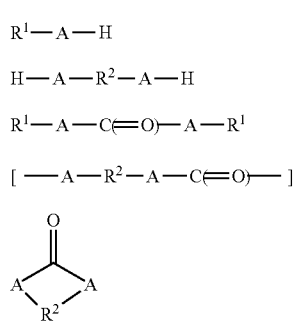 (II-2)

wherein
A is O, S or $NR^3$ wherein $R^3$ is H or a $C_{1-4}$ alkyl group, or $R^3$ forms a nitrogen-containing heterocyclic group with $R^1$ and N,
$R^1$ is a $C_{6-14}$ aryl group, a $C_{4-14}$ heteroaryl group or a $C_{2-24}$ alkylpolyoxyalkylene group,
$R^2$ is a $C_{2-10}$ alkylene group, a $C_{6-14}$ arylene group, a $C_{4-14}$ heteroarylene group or a $C_{2-24}$ polyoxyalkylene group, and the base is one or more bases selected from the group consisting of a heterocyclic aromatic amine, a non-nucleophilic strong base having a basicity ($pK_{BH+}$) in acetonitrile of 20 or more and an inorganic base.

2. The production method according to claim 1, wherein the $C_{1-4}$ halogenated hydrocarbon is a $C_{1-4}$ polyhalogenated hydrocarbon.

3. The production method according to claim 1, wherein the $C_{1-4}$ halogenated hydrocarbon is chloroform.

4. The production method according to claim 1, wherein the heterocyclic aromatic amine is pyridine, picoline or lutidine.

5. The production method according to claim 1, wherein the non-nucleophilic strong base is 1,5,7-triazabicyclo[4.4.0]dec-5-ene, 7-methyl-1,5,7-triazabicyclo[4.4.0]dec-5-ene, 1,8-diazabicyclo[5.4.0]undec-7-ene, 1,5-diazabicyclo[4.3.0]non-5-ene or 1,1,3,3-tetramethylguanidine.

6. The production method according to claim 1, wherein the inorganic base is an alkali metal hydroxide, an alkali metal hydrogen carbonate or an alkali metal carbonate.

7. The production method according to claim 1, wherein 0.001 times or more by mole and 1 time or less by mole of the nucleophilic functional group-containing compound is used to the $C_{1-4}$ halogenated hydrocarbon.

8. The production method according to claim 1, wherein 1.5 times or more by mole and 10 times or less by mole of the base is used to the nucleophilic functional group-containing compound.

9. The production method according to claim 1, wherein a wavelength of the light irradiated on the composition is 180 nm or more and 500 nm or less.

* * * * *